(12) United States Patent
Atkinson et al.

(10) Patent No.: US 7,797,053 B2
(45) Date of Patent: Sep. 14, 2010

(54) LEAD STABILIZATION DEVICES AND METHODS

(75) Inventors: Robert E. Atkinson, White Bear Lake, MN (US); Peter T. Keith, St. Paul, MN (US); Michael Berman, Minnetonka, MN (US)

(73) Assignee: Aetherworks, Inc., White Bear Lake, MN (US)

( * ) Notice: Subject to any disclaimer, the term of this patent is extended or adjusted under 35 U.S.C. 154(b) by 649 days.

(21) Appl. No.: 11/139,894

(22) Filed: May 27, 2005

(65) Prior Publication Data

US 2006/0009830 A1    Jan. 12, 2006

Related U.S. Application Data

(63) Continuation of application No. PCT/US2004/033156, filed on Oct. 8, 2004, and a continuation-in-part of application No. 10/736,863, filed on Dec. 16, 2003, now abandoned.

(60) Provisional application No. 60/576,368, filed on Jun. 2, 2004, provisional application No. 60/510,663, filed on Oct. 10, 2003.

(51) Int. Cl.
*A61N 1/05* (2006.01)

(52) U.S. Cl. .................................. 607/115; 607/126
(58) Field of Classification Search ............... 607/115, 607/122–128; 604/164.13, 165.01–165.04; 600/585

See application file for complete search history.

(56) References Cited

U.S. PATENT DOCUMENTS

| | | | |
|---|---|---|---|
| 4,628,944 A | 12/1986 | MacGregor et al. | |
| 4,989,617 A * | 2/1991 | Memberg et al. | 607/116 |
| 5,071,407 A | 12/1991 | Termin et al. | |
| 6,516,230 B2 * | 2/2003 | Williams et al. | 607/116 |
| 7,386,351 B2 * | 6/2008 | Hine et al. | 607/122 |
| 2002/0147487 A1 | 10/2002 | Sundquist et al. | |
| 2002/0161423 A1 | 10/2002 | Lokhoff et al. | |
| 2003/0023295 A1 * | 1/2003 | Osypka | 607/122 |
| 2003/0032936 A1 * | 2/2003 | Lederman | 604/507 |
| 2003/0153966 A1 * | 8/2003 | Taubert et al. | 607/122 |
| 2005/0033394 A1 * | 2/2005 | Seifert et al. | 607/125 |

* cited by examiner

*Primary Examiner*—Michael Kahelin
(74) *Attorney, Agent, or Firm*—Robert E. Atkinson

(57) ABSTRACT

Devices and methods for stabilizing an electrical lead in a cardiac vein of a heart using a tether and a stent anchor. The stent anchor may include a proximal eccentric apex such that the distal electrode of the lead lies against and establishes electrical contact with tissue of the heart.

2 Claims, 13 Drawing Sheets

LEAD STABILIZATION DEVICES AND METHODS

CROSS REFERENCE TO RELATED APPLICATION

This is a continuation of PCT/US04/033156, filed on Oct. 8, 2004, which claims priority to U.S. Provisional Application No. 60/576,368, filed Jun. 2, 2004, and is a Continuation-in-Part of U.S. patent application Ser. No. 10/736,863 filed on Dec. 16, 2003 now abandoned, which claims priority to U.S. Patent Application No. 60/510,663, filed Oct. 10, 2003, all of which are hereby incorporated by reference herein.

FIELD OF THE INVENTION

The present invention generally relates to medical devices and methods. More specifically, the present invention relates to medical devices and methods for stabilizing leads in cardiac vasculature.

BACKGROUND OF THE INVENTION

Heart failure is an increasingly common condition worldwide. Cardiac resynchronization therapy (CRT) has shown great promise as a treatment for a large percentage of patients in various stages of heart failure. CRT involves cardiac pacing of both the left and right ventricles of the heart (biventricular pacing), which causes both ventricles to beat simultaneously, greatly improving the pumping efficiency of the heart. Typically, the lead that stimulates the left ventricle is positioned via the coronary sinus into a cardiac vein along the free wall of the left ventricle.

There are numerous challenges in successfully positioning the left ventricular lead, including accessing the coronary sinus and veins, advancing the leads to a position which yields proper stimulation, and preventing subsequent lead dislodgement during removal of delivery devices. Post procedural challenges related to the left ventricular lead include lead dislodgement prior to fibrosis, loss of stimulation capture, and lead removal necessitated by infection.

Currently available left ventricular leads have generally been designed to facilitate effective delivery and provide fatigue resistance, and are particularly susceptible to dislodgement both intra-procedurally and post-procedurally. Efforts to incorporate more aggressive anchoring into the lead body have generally been insufficient for preventing dislodgment, and/or have compromised effective delivery, fatigue resistance and subsequent lead removal.

SUMMARY OF THE INVENTION

Therefore, a need exists to enable effective lead stabilization without compromising lead delivery, resistance to lead fatigue, or lead removal. To address this need, various exemplary non-limiting embodiments are described herein which provide devices and methods for acute and/or chronic lead stabilization. By way of example, not limitation, the lead stabilization mechanisms described herein may be separate from but cooperative with the lead, thus allowing independent delivery and function. To this end, the lead may be designed for effective delivery and fatigue resistance, and the stabilization mechanism may be designed for effective acute and/or chronic anchoring to prevent lead dislodgement. In addition, the stabilization mechanisms described herein may be separable from the lead to permit subsequent lead removal.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
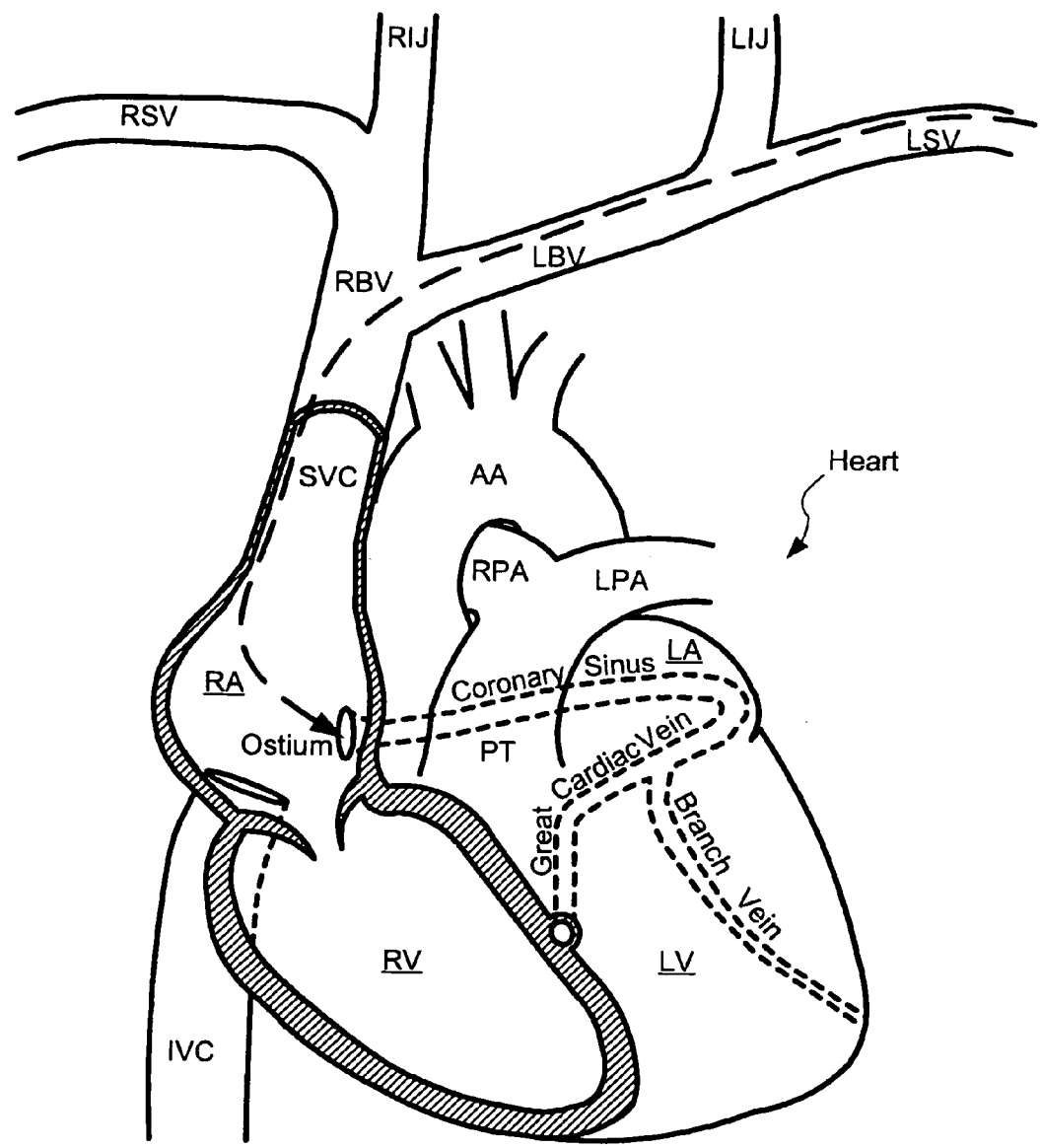
FIG. 1 is an anterior view of a human heart and associated vasculature.
Figure 2:
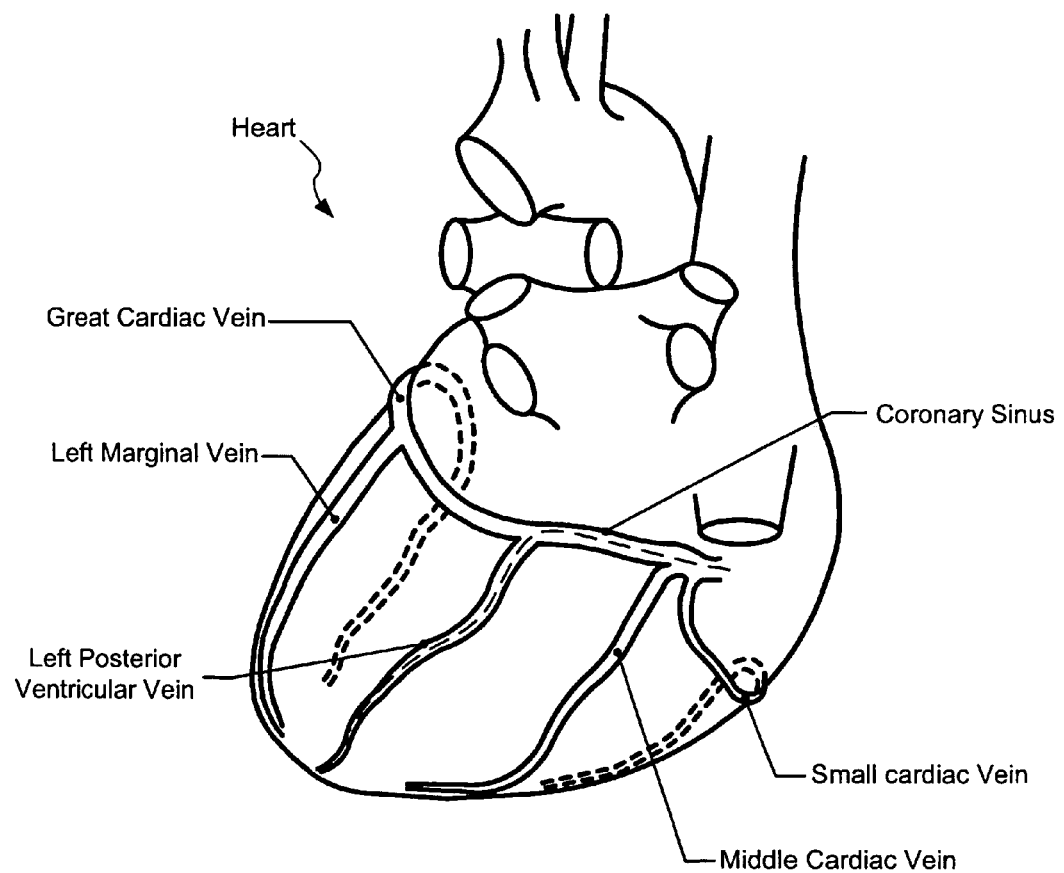
FIG. 2 is a posterior view of a human heart and associated cardiac venous vasculature.

With reference to FIGS. 1 and 2, the anatomy of a human heart (H) is illustrated. FIG. 1 shows the heart from the anterior side, with the right chambers of the heart shown in section. FIG. 2 shows the heart from the posterior side, and illustrates the cardiac veins, including the coronary sinus (CS) and its associated venous branches (great cardiac vein, left marginal vein, left posterior ventricular vein, middle cardiac vein, and small cardiac vein). The CS carries the primary venous return for the cardiac circulation, with the venous branches distributed about the heart and draining into the CS. The CS circumnavigates the left side of the heart, generally between the left atrium (LA) and the left ventricle (LV). The CS drains into the right atrium (RA) at the ostium.

Left ventricular leads are typically implanted with the proximal end connected to a pulse generator in a subcutaneous or submuscular pocket, and the distal end (electrode(s)) disposed in one of the cardiac veins to stimulate the left ventricle. The lead body typically extends from the pulse generator in the subcutaneous or submuscular pocket, through the vein wall and into the left subclavian vein (LSV), through the left brachio-cephalic vein (LBV), down the superior vena cava (SVC) and into the right atrium (RA), into the CS and into the target cardiac vein. The venous circulation is usually accessed by introducing delivery catheters (called guide catheters or guide sheaths) from a venous arteriotomy in the LSV to the CS ostium, following the dashed line shown in FIG. 1. Once the CS is cannulated by a delivery catheter, a coronary venogram is obtained to visualize the cardiac veins. The lead is advanced into the CS and the desired cardiac vein, following an exemplary path indicated by the dashed line shown in FIG. 2.

There are generally two categories of LV leads, over-the-wire (OTW) leads and stylet-delivered leads. OTW leads incorporate a guide wire lumen which extends through the entire lead body, emerging at the tip of the lead. Navigation within the CS and cardiac veins is performed by advancing a steerable guide wire to a desired location in a cardiac vein, and the lead is then advanced over the guide wire. Stylet delivered leads have a stylet lumen which extends through the lead body, but typically terminates proximal of the distal tip. A shaped styled is positioned in the stylet lumen and the lead and stylet are advanced together to navigate the lead to a desired location in a cardiac vein.

Once the lead is positioned in a location that yields acceptable stimulation (capture), the delivery catheter is removed. Depending on the particular lead, and the type of electrical connector utilized, removal is accomplished either by withdrawing the delivery catheter over the proximal end of the lead, or by splitting the delivery catheter as it is removed over the proximal end of the lead. In some situations, removal of the delivery catheter may dislodge the lead, as the stability of the lead position is often quite tenuous. Even if the lead is not dislodged during removal of the delivery catheter, the beating of the heart and other patient activities can cause lead movement or dislodgement, leading to potential loss of capture (effective pacing of the LV).

Figure 3:
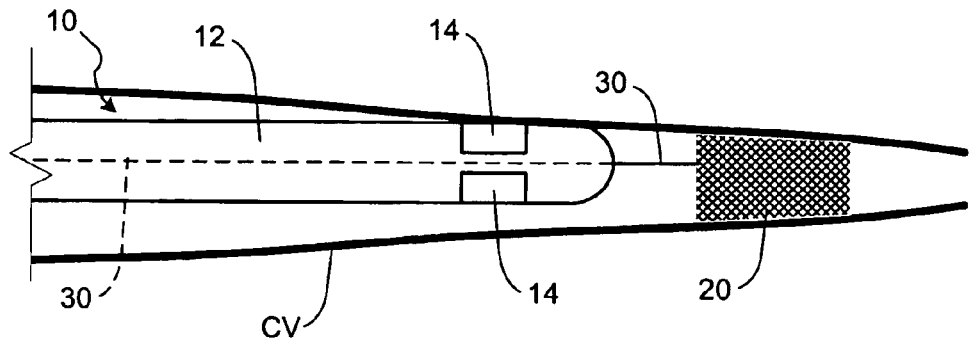
FIG. 3 is a schematic side view of a lead and an anchor device in the form of a stent disposed in a cardiac vein.

With reference to FIG. 3, a pacing lead 10 and an anchor device in the form of a stent 20 are schematically shown disposed in a cardiac vein CV. Generally, the CV generically refers to venous braches of the coronary sinus such as the great cardiac vein, left posterior ventricular vein, middle cardiac vein, small cardiac vein, or other cardiac vein that leads to the left ventricle, and preferably that leads to the apex of the left ventricular free wall or that otherwise provides for effective pacing of the left ventricle. Those skilled in the art will recognize that because of anatomic variation, the precise name and position of the CV will vary.

Lead 10 may comprises a conventional pacing lead having an elongate body or shaft 12 and one or more electrodes 14 connected to a pulse generator (not shown) by corresponding wires or traces inside the lead body 12. Lead 10 is generally designed to be very flexible and fatigue resistant to permit free cardiac movement, to minimize tissue trauma, and to withstand repeated flexure primarily caused by the beating heart. The electrodes 14 are typically positioned on or near the wall of the vein facing the heart to establish effective conduction into the heart wall.

Stent 20 may be self-expandable or balloon expandable, for example, and may be formed of a biocompatible metal material such as stainless steel, Nitinol, Elgiloy, or MP35N. Alternatively, stent 20 may be formed of a biodegradable polymeric material such as poly-L-lactic acid, polyglycolic acid, or polycaprolactone, or other biodegradable materials such as those used for biodegradable sutures. In the case of polymeric materials used for stent 20, the polymer may be loaded with a radiopaque agent such as barium, bismuth subcarbonate, etc. to facilitate x-ray visualization. Generally speaking, all of the anchors of the anchor devices described herein may be formed of the aforementioned materials and may be radiopaque. Additionally, all or portions of the anchors 20 described herein may have surface modifications to increase friction and/or to promote tissue in-growth.

Stent 20 may be connected to lead 10 by an elongate connector 30. Elongate connector 30 may comprise a tether that is flexible and fatigue resistant, including monofilament and multifilament polymeric constructions. For example, the tether 30 may comprise a braided cord of a high strength biocompatible polymer such as polyester, polypropylene, or polyethylene (e.g., Spectra brand). The tether 30 may be partially or fully covered or coated with a material that promotes tissue in-growth such as ePTFE. The tissue in-growth promoting material may serve to secure the elongate member 30 to the lead 10 and/or prevent bacteria migration along the elongate member 30.

In the embodiment illustrated in FIG. 3, the elongate member or tether 30 extends through the lumen (e.g., guide wire lumen) of the lead 10. This embodiment is particularly suitable for OTW leads that typically have a guide wire lumen extending therethrough. Accordingly, the tether 30 may have an outside diameter that is less than the inside diameter of the guide wire lumen of the lead 10, such as 0.004 to 0.016 inches, for example.

The proximal end of the tether 30 may extend out the proximal end of the lumen of the lead 10, and may be connected to the lead 10 by tying a knot that is larger than the diameter of the lumen, for example. Alternatively, the proximal end of the tether 30 may be connected to the proximal end of the lead 10 by trapping the tether 30 in the lumen of the lead 10 with a wedge or pinching it between the electrical connector of the lead 10 and the socket of the pulse generator. The distal end of the tether 30 may be connected to the stent 20 by tying the tether 30 in a knot around a strut of the stent 20, or swaging and end of the tether 30 between struts of the stent 20, for example.

In this embodiment, the stent 20 and tether 30 may be deployed before the lead 10 is delivered. The stent 20 may be deployed in a distal portion of the target CV with a delivery device as described in more detail with reference to FIG. 6. Once deployed, the proximal end of the tether 30 may be inserted into the distal end of the lumen extending through the lead 10, and the lead 10 may then be advanced over the tether 30 and into the CV to the desired position, and pacing tests may be performed to ascertain LV pacing capture. Once the lead 10 is in the desired position, the proximal end of the tether 30 may be secured to the proximal end of the lead 10 as described previously.

If it is necessary or desired to remove or reposition the lead 10, the lead 10 may be removed from the CV by disconnecting the tether 30 from the lead 10 (e.g., by cutting the knot in the tether 30 at the proximal end of the lead 10), the tether 30 may be removed from the CV by disconnecting the tether 30 from the stent 20 (e.g., by using a cutting device as described in more detail with reference to FIG. 12), and the stent 20 may be left in place in the CV without compromising blood flow through the CV.

Figure 4:
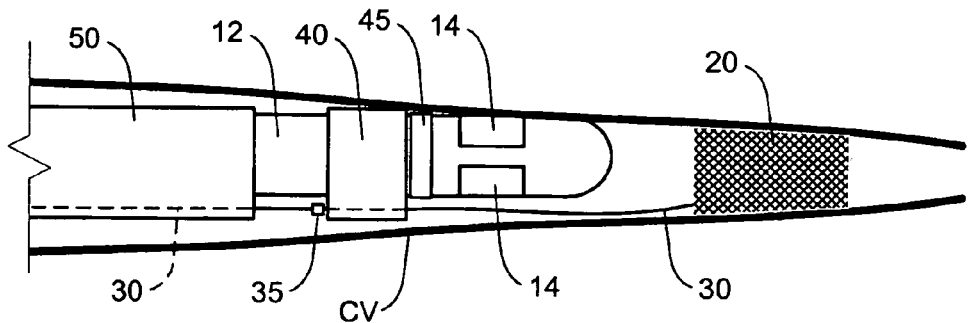
FIG. 4 is a schematic side view of a lead and an alternative anchor device in the form of a stent disposed in a cardiac vein.

With reference to FIG. 4, an alternative anchor device arrangement is shown schematically. In this embodiment, rather than extending through the lumen of the lead 10, the tether 30 extends along side the lead 10. This embodiment is particularly suitable for stylet-delivered leads that typically do not have a lumen extending therethrough, but may be used with either stylet-delivered or OTW leads. This embodiment also allows for the delivery of the anchor device either before or after lead 10 placement.

The tether 30 may be connected to the lead 10 by a fastener such as collar 40. Collar 40 may comprise a short dual lumen tube including a relatively large lumen to accommodate the lead 10 therethrough and a relatively small lumen to accommodate the tether 30 therethrough. Collar 40 may be fixedly connected to the lead 10 if the anchor device is delivered prior to the lead 10 by swaging, adhesive, etc. To facilitate delivery of the lead after placement of the lead 10, the collar 40 may be slidable over the lead 10 and lock in place adjacent the distal potion of the lead 10 using a mating geometry such as a detent on the outer surface of the lead 10 that receives a protrusion extending from the inside surface of the collar 40. Alternatively, the outer surface of the lead 10 may include a protrusion such as a stepped ridge 45 that abuts the distal end of the collar 40 as the collar 40 is advanced over the lead 10 in order to prevent proximal movement of the lead 10 relative to the collar 40. With this alternative, the stepped ridge 45 may be an integral extension of the outer surface of the lead 10 or a separate component fixedly connected to the lead 10.

The tether 30 may be effectively connected to the collar 40 to prevent proximal movement of the collar 40 relative to the tether 30 by utilizing a knot or stop 35 that is slid down the length of the tether 30. A knot may be made in the tether at its proximal end and advanced distally to the collar 40 using a conventional knot pusher. A stop 35 may be used and configured to readily advance distally over the tether 30 and resist retraction proximally. For example, stop 35 may comprise a short tubular segment having proximal facing flanges extending from the inside surface that selectively engage the tether 30 only when the stop 35 is advanced in the proximal direction relative to the tether 30. To facilitate removal of the lead 10, the stop 35 may be cut or the tether 30 may be cut between the stop 35 and the collar 40 using the cutting device described with reference to FIG. 12.

To facilitate advancement of the collar 40 over the lead 10 and to facilitate advancement of the stop 35 over the tether 35, a dual lumen advancement sheath 50 may be slid (pushed) over the lead 10 and tether 30. Sheath 50 may comprise an elongate dual lumen tube having a length sufficient to extend over the lead 10, through the venous vasculature, and out the venous access site, with one lumen to accommodate the lead 10 and another lumen to accommodate the tether 30. Sheath 50 may include a slit (not shown) along the length thereof to facilitate peeling over the lead 10. Sheath 50 may be removed over the lead 10 and tether 30 after advancement of the collar 40 and stop 35, or it may be left implanted to contain the tether 30 relative to the lead 10.

Figure 5:
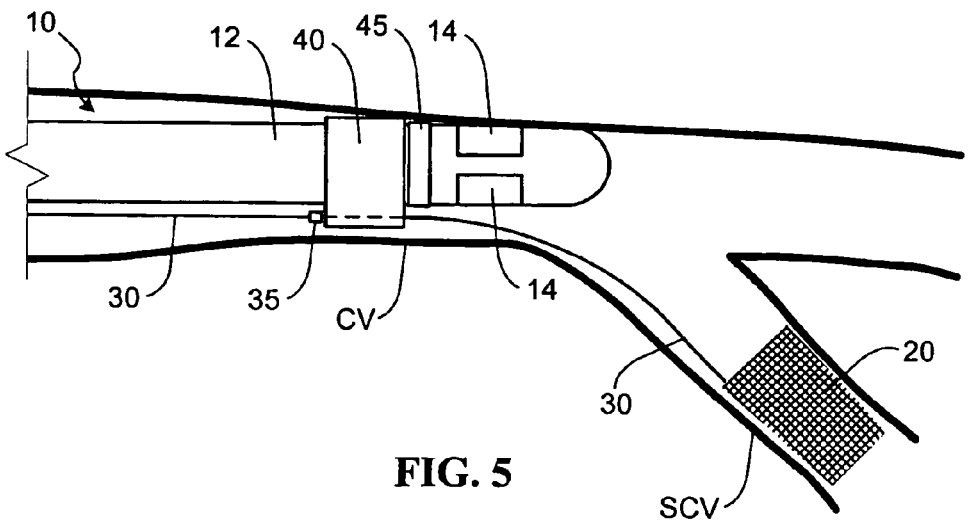
FIG. 5 is a schematic side view of a lead disposed in a coronary vein and an alternative anchor device in the form of a stent disposed in a secondary cardiac vein.

With reference to FIG. 5, an alternative anchor device arrangement is shown schematically. In this embodiment, the stent 20 is deployed in a secondary cardiac vein (SCV) and connected via tether 30 and collar 40 to lead 10 as described with reference to FIG. 4. Positioning the stent 20 in a SCV enhances the anchoring effect and, because of collateral venous circulation, reduces the possibility of adverse effects if the stent 20 were to become occluded.

Figure 6:
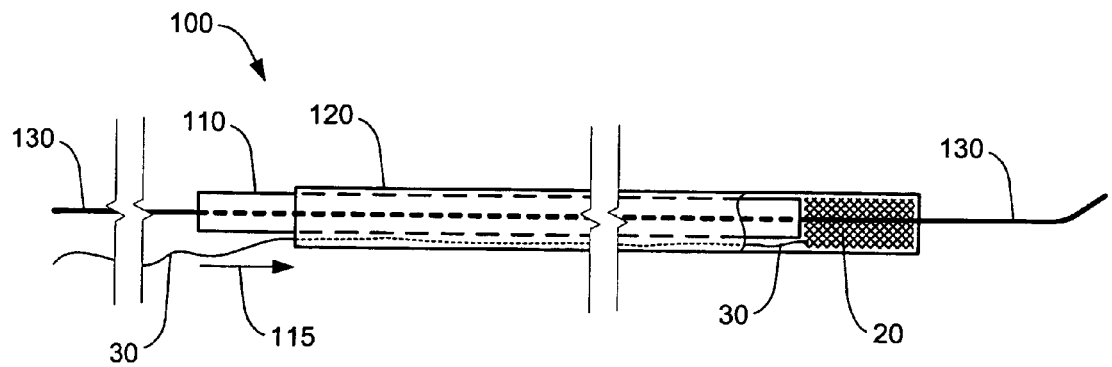
FIG. 6 is a schematic side view of an anchor delivery device for use in delivering the anchor devices illustrated in FIGS. 3-5.

With reference to FIG. 6, a schematic side view of an anchor delivery catheter device 100 for use in delivering anchor devices such as stent 20 as described in connection with the embodiments of FIGS. 3-5. In this embodiment, the delivery device 100 is configured to deliver an elastically expandable (self-expanding) stent, but a balloon catheter type delivery device may alternatively be utilized to deliver a plastically deformable (balloon expandable) stent. In the illustrated embodiment, the delivery catheter 100 may include an inner tube 110 coaxially disposed in an outer tube 120. The stent 20 may be pre-loaded inside the outer tube 120, near its distal end. The distal end of the inner tube 110 abuts the proximal end of the stent 20, and may be advanced distally with respect to the outer tube 120 as indicated by arrow 115 to advance stent 20 out of the distal end of the outer tube 120. The tether 30 may be disposed between the inner tube 110 and the outer tube 120.

One or more sensing or test electrodes (not shown) may be disposed on a distal portion of the outer tube 120, with corresponding wires extending proximally therefrom for connection to an ECG monitor or an external pulse generator. The sensing or test electrode(s) may be used to measure ECG signals and/or deliver pacing signals in order to electrically map the CS and/or CV, and/or to determine a desirable position for the lead electrodes 14, preferably prior to deployment of the stent anchor 20. The use of such sensing or test electrodes may be incorporated into other delivery anchor device systems described elsewhere herein.

To facilitate delivery, a guide wire 130 may be used to initially navigate the CV. Once the guide wire 130 is in the desired position, the delivery catheter 100 with the pre-loaded stent 20 therein may then be advanced over the proximal end of the guide wire 130 and advanced thereover to the desired deployment position. The inner tube 110 may be advanced in the distal direction with respect to the outer tube 120 as indicated by arrow 115 to deploy the stent 20 in the CV. Once the stent 20 is deployed, the delivery catheter 100 may be removed.

Figure 7:
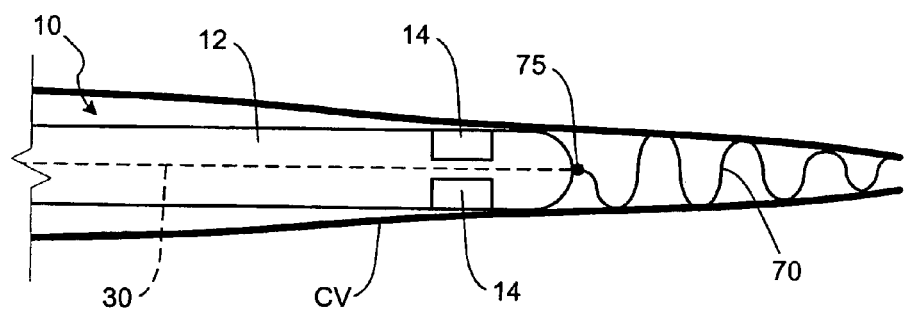
FIG. 7 is a schematic side view of a lead and an alternative anchor device in the form of a coil disposed in a cardiac vein.

With reference to FIG. 7, an alternative anchor device arrangement is shown schematically. In this embodiment, a coil 70 is deployed distal of the lead 10 and connected via tether 30 to lead 10 as described with reference to FIG. 3. The proximal end of the coil 70 may be connected to the distal end of the tether 30 at connection 75, and the coil 70 may comprise a resilient structure such as a metal wire formed of any of the materials described with reference to stent 20. Coil 70 may be delivered via a lumen (e.g. guide wire lumen) extending through the lead 10 and is particularly suitable for an OTW lead. The coil 70 may be advanced through the lumen of the lead 10 using a push tube (not shown) having sufficient column strength disposed over the tether 30 that abuts the connection 75 between the coil 70 and the tether 30.

To accommodate delivery through the lumen extending through the lead 10, the coil 70 may have a delivery configuration wherein the coil 70 is elongated to have a reduced profile sufficiently small to fit into the lumen, and a deployed configuration wherein the coil 70 is radially expanded to have an expanded profile sufficiently large to frictionally engage the wall of the CV. The coil 70 may be highly elastic such that it assumes the deployed configuration automatically upon advancement out of the distal end of the lead 10, or the coil may be actuated (e.g., thermally) upon advancement out of the distal end of the lead 10 to assume the deployed configuration.

Figure 8:
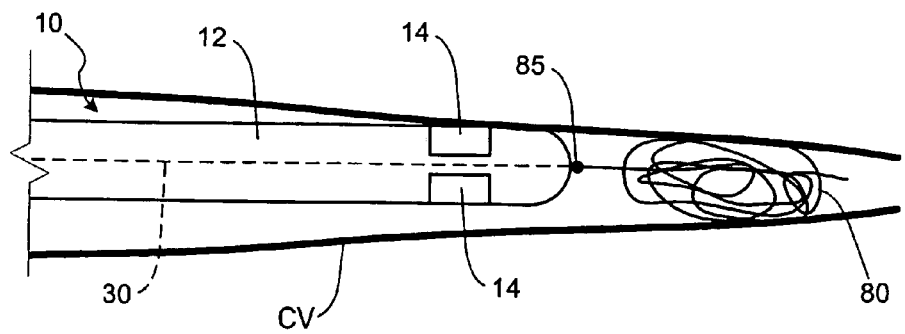
FIG. 8 is a schematic side view of a lead and an alternative anchor device in the form of a bundle disposed in a cardiac vein.

With reference to FIG. 8, an alternative anchor device arrangement is shown schematically. In this embodiment, a bundle 80 is deployed distal of the lead 10 and connected via tether 30 to lead 10 as described with reference to FIG. 3. The proximal end of the bundle 80 may be connected to the distal end of the tether 30 at connection 85, and the bundle 80 may comprise a resilient structure such as a metal wire formed of any of the materials described with reference to stent 20. Bundle 80 may be delivered in the same manner as and may have the same or similar characteristics as coil 70 described with reference to FIG. 7. Bundle 80, as opposed to coil 70, may have an occlusive effect, and therefore may be particularly suitable for a SCV to take advantage of collateral venous circulation.

Figure 9:
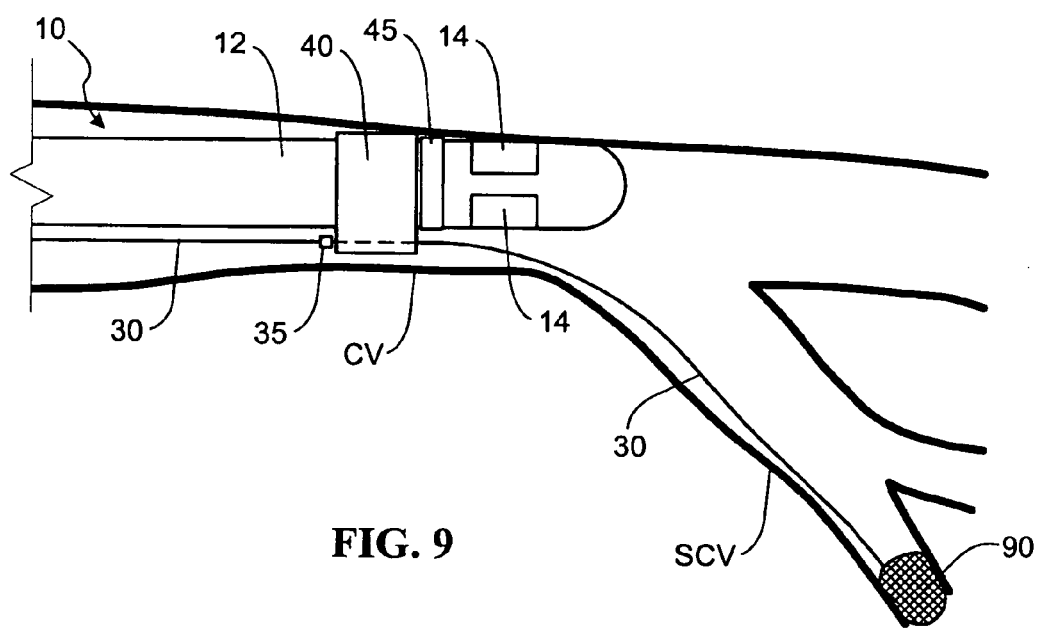
FIG. 9 is a schematic side view of a lead disposed in a cardiac vein and an alternative anchor device in the form of a plug disposed in a secondary cardiac vein.

With reference to FIG. 9, an alternative anchor device arrangement is shown schematically. This embodiment is similar to the embodiment illustrated in FIG. 5, except that a plug 90 is used in place of stent 20. The plug 90 may comprise a curable adhesive (e.g., cyanoacrylate, EVA in a DSMO solvent) or an embolic coil, for example, such as those conventionally used in occluding blood vessels and aneurisms. Plug 90 may be deployed in a SCV using a conventional embolic delivery system and connected via tether 30 and collar 40 to lead 10 as described with reference to FIG. 4. Positioning the plug 90 in a SCV enhances the anchoring effect, and despite the occlusive effect of the plug 90, the possibility of adverse effects are reduced if not eliminated due to collateral venous circulation.

Figure 10:
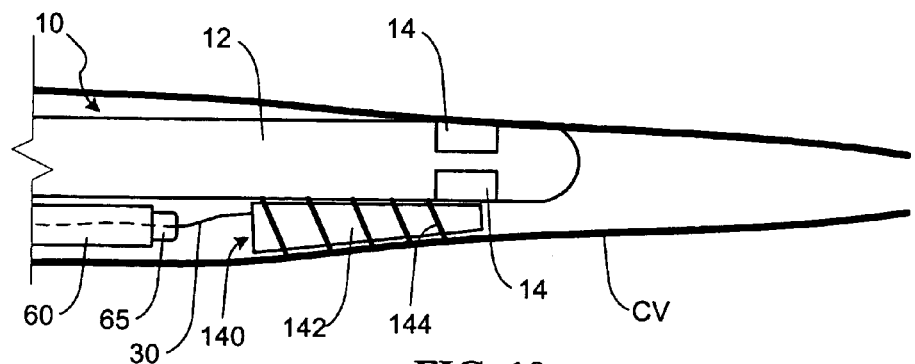
FIGS. 10 and 11 are schematic side views of a lead and alternative anchor devices in the form of wedges disposed in a cardiac vein.
Figure 11:
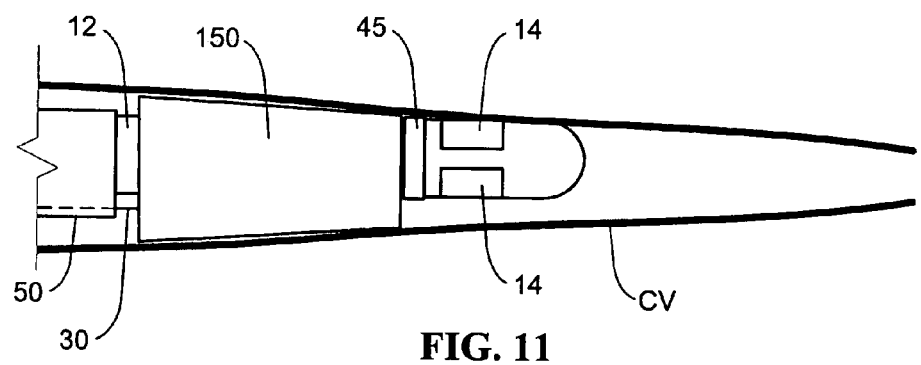

With reference to FIGS. 10 and 11, alternative anchor device arrangements are shown schematically. In these embodiments, a wedge 140 or 150 is deployed adjacent the distal portion of the lead 10, such as proximal of electrodes 14. Wedges 140 and 150 frictionally engage the lead body 12 and the wall of the CV, to lodge the lead 10 in the desired position in the CV. The wedges 140 and 150 may be connected to tether 30 to facilitate subsequent removal. Wedges 140 and 150 may comprise any of the materials discussed with reference to stent 20.

Wedges 140 and 150 are particularly suitable for deployment after the lead 10 has been delivered to the desired position, as shown in FIGS. 10 and 11. Alternatively, the wedges 140 and 150 may be deployed before the lead 10 has been delivered, with the wedges positioned distally of the desired position for the lead 10. In this alternative embodiment, the wedge may be over-sized with respect to the inside diameter of the CV where it is to be positioned in order to cause atraumatic expansion of the CV wall around the wedge, thus enhancing friction therebetween.

With specific reference to FIG. 10, wedge 140 includes a body portion 142 and optional threads 144. Body portion 142 may include a perfusion lumen extending therethrough to permit blood perfusion from the distal end to the proximal end of the wedge 140. The wedge body 142 (or the wedge threads 144 if used) may have a diameter slightly greater than the diameter of the lumen of the CV less the diameter of the lead 10 in order to provide a snug frictional fit therebetween. Wedge 140 may be delivered into the desired position utilizing a push tube 60 advanced over a guide wire (not shown), for example, wherein the push tube 60 has sufficient column strength to push the wedge 140 alongside the lead 10 with the distal end 65 of the push tube abutting the proximal end of the wedge 140 and the tether 30 extending through the push tube. The push tube may also have sufficient torsional strength with a distal end 65 that mates with the proximal inside diameter of the wedge 140 such that the wedge 140 may be rotated to engage or disengage the threads 144 with the lead 10 and the wall of the CV.

With specific reference to FIG. 11, wedge 150 comprises a short dual lumen having one lumen to accommodate the lead 10 and another (crescent shaped) lumen to permit blood perfusion from the distal end to the proximal end of the wedge 150. The wedge 150 may be tapered and may have a diameter slightly greater than the diameter of the lumen of the CV less the diameter of the lead 10 in order to provide a snug frictional fit therebetween. Stepped ridge 45 prevents proximal movement of the lead 10 relative to wedge 150 as described previously. Wedge 150 may be delivered into the desired position utilizing a push tube 50 advanced over the lead 10, as described previously.

Figure 12:
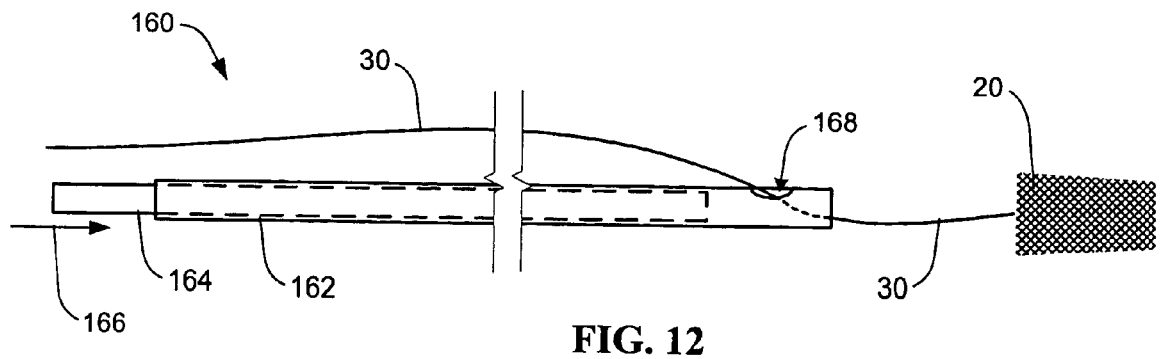
FIG. 12 is a schematic illustration of a release mechanism in the form of a connector cutter.

With reference to FIG. 12, a cutting device 160 is shown schematically. Cutting device 160 may be used to cut tether 30 and/or stop 35 in order to disconnect the tether 30 from the anchor device, such as stent 20. Cutting device 160 is merely an example of a variety of cutting mechanisms that may be used to sever the connection of the tether 30 from the anchor device. For example, the tether 30 may be equipped with two internal wires connected to a distal electrolytic fuse that separates (melts) upon the application of electrical current, such as those used for detachable embolic coils.

In this exemplary embodiment, cutting device 160 includes an outer tube 162 and an inner tube 164 coaxially disposed and movable therein. The outer and inner tubes 162 and 164 may have a length sufficient to extend from outside the vascular access site to the anchor device, and may be configured for intravascular navigation and advancement over tether 30. The distal end of the inner tube 164 may have a sharpened edge and may be formed of a material that retains a cutting edge (e.g., metal). A cutting hole 168 is provided adjacent the distal end of the outer tube 162 through which the tether 30 may be threaded. The distal circumference of the cutting hole 168 may be sharpened and may be formed of a material that retains a cutting edge (e.g., metal) After the cutting device is advanced over the tether 30 to the desired cutting site, the inner tube 164 may be advanced distally as indicated by arrow 166, with the sharpened distal end of the inner tube 164 and the sharpened cutting hole 168 acting as shears to cut the tether 30 at the cutting hole 168.

Figure 13:
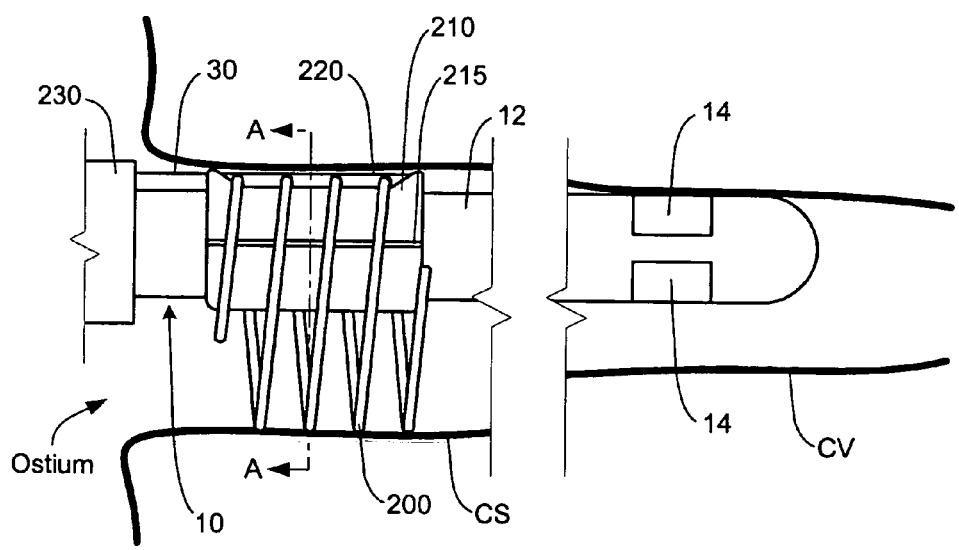
FIG. 13 is a schematic side view of a lead disposed in a cardiac vein and an anchor device in the form of a coiled stent disposed near the ostium of the coronary sinus.
Figure 13A:
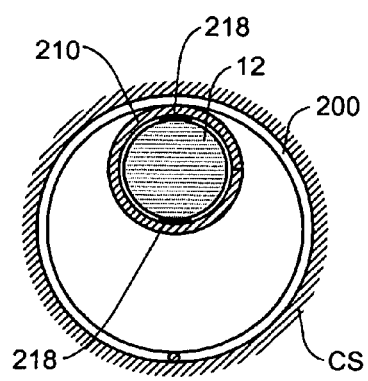
FIG. 13A is a cross sectional view taken along line A-A in FIG. 13.

With reference to FIG. 13, a lead 10 is shown disposed in a CV, with an anchor device in the form of a coiled stent 200 disposed near the ostium of the CS. The coiled stent 200 may be positioned near the ostium of the CS, where the vessel diameter is large enough to resist becoming occluded by the presence of the coiled stent 200 next to the lead 10. However, it is contemplated that the coiled stent 200 may be placed elsewhere within the CS or CV in which the lead is positioned. As seen in FIG. 13A, the lead 10 is eccentrically disposed in the lumen of the CS to define a relatively large crescent shaped blood perfusion lumen.

Coil stent 200 may be formed of a resilient material such as Nitinol, Elgiloy, MP35N, or stainless steel. Coiled stent 200 could also be formed of degradable materials such as those described in reference to stent 20 above. Coiled stent 200 may be releasably attached to the lead 10 utilizing collar 210, and collar 210 may frictionally engage the body 12 of lead 10, thus facilitating anchoring of the lead within the coronary sinus or cardiac vein.

Figure 13B:
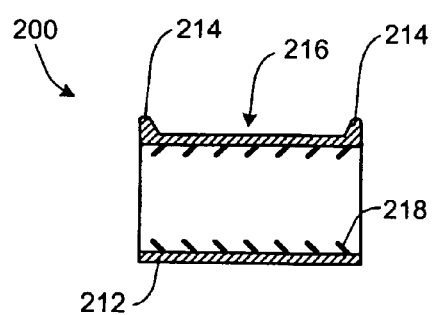
FIG. 13B is side sectional view of the fastener illustrated in FIG. 13.

With reference to FIG. 13B, the collar 210 may comprise a relatively short tube 212, and may include one or more proximally oriented grips 218. Grips 218 may be in the shape of finger-like projections, or circular ribs either partially or completely extending circumferentially around the inside of tube 212. Grips 218 facilitate the advancement of the collar 210 in a distal direction for delivery over lead 10, but resist proximal movement once the collar 210 is positioned in a desired anchoring location. Grips 218 may be formed of a soft resilient material such as silicone, polyurethane, polyether-block-amide, or the like.

To facilitate subsequent removal of the lead 10, the coiled stent 200 may be connected to the collar 210 in a detachable manner. For example, the coiled stent 200 may be connected to the collar 210 utilizing a biodegradable adhesive connecting adjacent portions of the coil 200 to the collar 210. Such an adhesive may degrade after the lead 10 has chronically anchored to the wall of the CS by normal tissue encapsulation. After the adhesive has degraded, the lead 10 (along with collar 210) may be removed utilizing standard techniques, with the coiled stent 200 remaining in the CS.

Alternatively, the coiled stent 200 may be secured to the collar 210 utilizing a retractable pin 220. In this alternative embodiment, collar 210 may include two angled flanges 214 collectively defining a recess 216 in which stent coil 200 may reside. Pin 220 may span the length of the recess 216 between the flanges 214, extending over the coiled stent 200 to retain the coil stent 200 in the recess 216, thus providing a connection between the stent coil 200 and the collar 214. Subsequent release of the stent coil 200 from the lead 10 may be accomplished by removing pin 220 using tether 30 which extends from the proximal end of the lead 10 to the pin 220. The proximal end of the pin 220 is connected to the distal end of the tether 30, and the pin 220 may be removed by pulling the tether 30 proximally. After the pin 220 is removed, the lead 10 and collar 210 are free from the stent coil 200 and may be removed with standard techniques, leaving stent coil 200 in the CS.

Delivery and deployment of the stent coil 200 and collar 210 may be facilitated by deployment sheath 230. The deployment sheath 230 may comprise a tubular catheter, having a lumen extending therethrough to accommodate the lead 10 and the stent coil 200. Alternatively, the lumen in the deployment sheath 230 may extend from a distal opening to a mid-shaft opening as used in conventional monorail style balloon catheters. After lead 10 has been positioned by standard techniques to a desired position, the stent coil 200 and collar 210 may be loaded on the proximal end of the lead 10. Coil 200 may be initially in a compressed condition, and loaded in the inside of the deployment sheath 230. If the lead 10 has a large diameter proximal connector, an optional slit 215 may be provided in the collar 220 to facilitate loading over the large diameter connector. In this case, the collar 210 and coil 200 may be positioned on the lead body 12 before the coil 200 is loaded into the deployment sheath 230. The deployment sheath 230 may be advanced distally down the body 12 of the lead 10 until the stent coil 200 and collar 210 are in the desirable location. The deployment sheath 230 may then be withdrawn proximally, with the collar 210 and stent coil 200 remaining in position on the lead 10 due to grips 218 on collar 210. As the stent coil 200 emerges from the deployment sheath 230, it expands to engage the wall of the CS. The deployment sheath 230 can then be removed from the lead 10.

Figure 14:
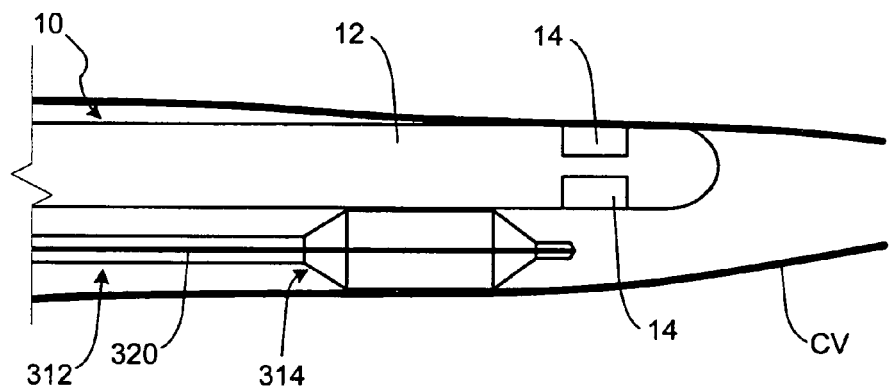
FIG. 14 is a schematic side view of a lead disposed in a cardiac vein and an anchor device in the form an anchor catheter.
Figure 15:
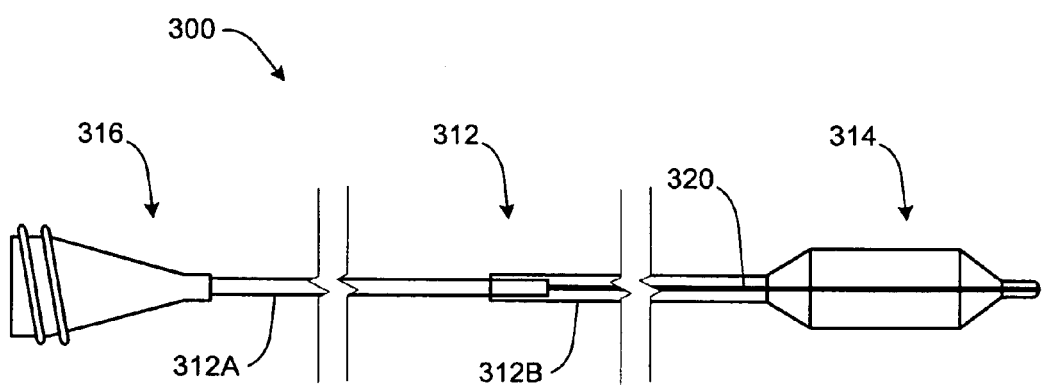
FIG. 15 is a detailed schematic view of the anchor catheter illustrated in FIG. 14.

FIGS. 14 and 15 illustrate an anchor device in the form of an anchoring catheter 300, which may be utilized to secure the position of lead 10, particularly during the removal of the guide sheath (guide catheter) used in the delivery of the lead 10. As described above, the lead stability is particularly vulnerable during the removal of the guide sheath.

In use, the anchoring catheter 300 is positioned next to the lead 10 after lead 10 has been positioned in a desired location. Anchoring catheter 300 may be advanced within the guide sheath (not shown), generally parallel to the lead body 12, or may be advanced outside the guide sheath. An expandable member such as a balloon 314 is inflated to frictionally secure lead 10 against the wall of the blood vessel. The guide sheath can then be removed without inadvertent dislodgement of the lead 10. The anchoring catheter 300 can then be removed. Since anchoring catheter 300 is next to and not surrounding the lead body 12, removal of the anchoring catheter 300 does not pose a risk of dislodging lead 10.

With particular reference to FIG. 15, anchoring catheter 300 is shown in more detail. Shaft 312 may comprise a proximal shaft portion 312A connected by adhesive, for example, to a distal shaft portion 312B. A luer adaptor 316 may be connected to the proximal end of the proximal shaft portion 312A for connection to an inflation apparatus (not shown) such as a syringe. An inflatable balloon 314 may be connected to the distal end of the distal shaft portion 312B, and may be formed of elastomeric material or a molded inelastic material.

Proximal shaft portion 312A may be relatively stiff and may be formed of a metallic tube such as a stainless steel hypotube. Distal shaft portion 312B may be relatively flexible and may be formed of a polymeric tube, for example. To facilitate advancement of the flexible distal shaft portion 312B and the balloon 314, a core wire may be connected to and extend from the distal end of the proximal shaft portion 312A. The core wire 320 may comprise a metal wire such as a tapered stainless steel mandrel.

Core wire 320 extends to the distal end of the balloon 314, and may extend beyond with an atraumatic spring tip, for example. The distal end of the balloon 314 may be bonded to the core wire 320, and the proximal end of the balloon 314 may be bonded to the distal end of the distal shaft portion 312B. Within the shaft 312 is a lumen through which inflation medium is infused to inflate balloon 314.

With general reference to FIGS. 16A-16E, various embodiments of retrievable anchor devices are shown in expanded state. These retrievable (i.e., repositionable and/or removable) designs are similar to the self-expanding stent anchor embodiment described with reference to FIGS. 3 and 6, the general aspects of which may be applied hereto. In each of the illustrated embodiments, the self-expanding anchor 20 is configured to be collapsed and retracted into a retrieval tube 128 (similar to outer tube 120) by pulling proximally on the tether 30 and/or by pushing distally on the retrieval tube 128. Alternatively, a pull chord (not shown) separate from the tether 30 may be used to collapse and retract the anchor 20 into the retrieval tube 128. In this alternative embodiment, the pull chord may be connected to a proximal end of the anchor 20 and the tether 30 may be connected to the anchor 20 distal of the proximal end thereof. The retrieval tube 128 may have a distal inside taper or funnel shape to facilitate collapse of the self-expanding anchor 20 when pulled therein.

Figure 16A:
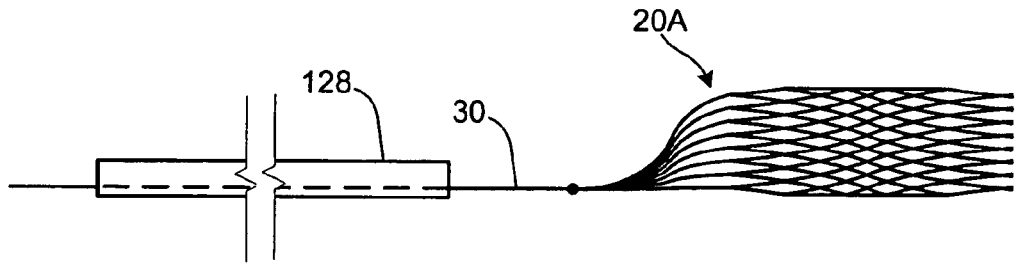
FIGS. 16A-16E are schematic side views of various retrievable anchor devices.

With specific reference to FIG. 16A, the retrievable anchor 20 may comprise a self-expanding braided structure 20A. The braided structure 20A is expanded in its relaxed state and may be compressed to fit into the delivery tube 120 or retrieval tube 128. The braided anchor 20A may include a plurality (e.g., eight or more) of highly flexible and elastic elongate members formed of a metal (e.g., stainless steel, Nitinol, Elgiloy, or MP35N), for example, that cross over and under each other in a braid pattern. The distal ends of the elongate members may be fused in pairs and/or shaped to face inwardly to provide an atraumatic distal edge. The proximal ends of the elongate members may be connected to the tether 30 to facilitate collapse and retraction into the retrieval tube 128.

Figure 16B:
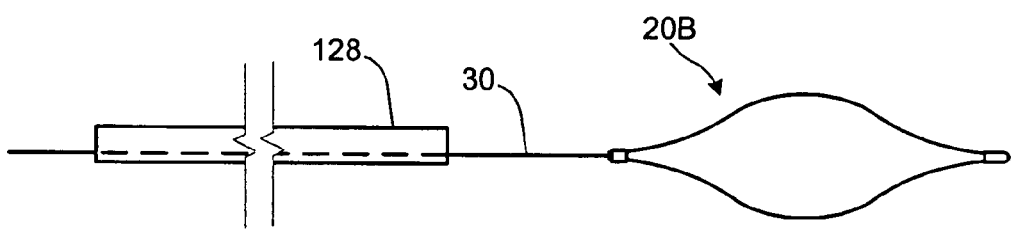
Figure 16C:
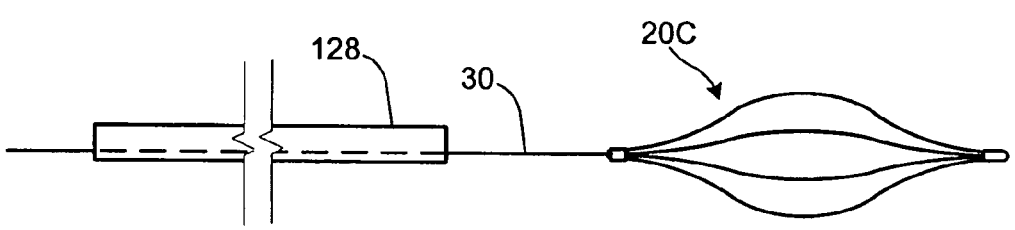

With reference to FIGS. 16B and 16C, the retrievable anchor 20 may comprise a self-expanding snare-like structure 20B or a self-expanding stone basket-like structure 20C, respectively. The snare-like 20B or basket-like 20C structures may include a plurality (e.g., two or more) of highly flexible and elastic elongate members formed of a metal (e.g., stainless steel, Nitinol, Elgiloy, or MP35N), for example, that extend generally parallel, do not cross, and bow outwardly. The snare-like 20B or basket-like 20C structures are expanded in their relaxed state and may be compressed to fit into the delivery tube 120 or retrieval tube 128. The distal ends of the elongate members may be fused together to provide an atraumatic distal tip, and the proximal ends of the elongate members may be connected to the tether 30 to facilitate collapse and retraction into the retrieval tube 128.

Figure 16D:
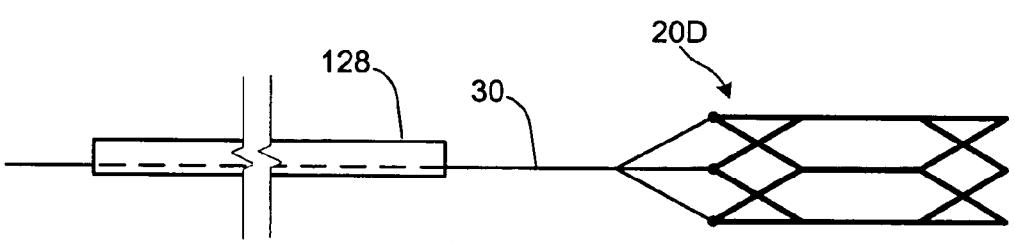

With reference to FIG. 16D, the retrievable anchor 20 may comprise a self-expanding stent 20D formed of a cut super elastic hypotube, for example. The self-expanding stent 20D is expanded in its relaxed state and may be compressed to fit into the delivery tube 120 or retrieval tube 128. The self-expanding stent 20D may be laser cut from a metallic (e.g., stainless steel, Nitinol, Elgiloy, or MP35N) hypotube, for example, having almost any desired pattern. In the illustrated embodiment, the self-expanding stent 20D has two sets of four diamonds interconnected by four middle struts. The proximal set of four diamonds provide a four point crown, to which a parachute-like tether 30 may be connected to facilitate collapse and retraction into the retrieval tube 128.

Figure 16E:
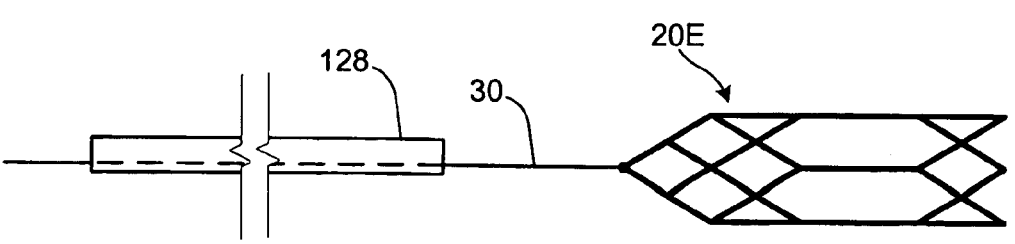

With reference to FIG. 16E, the retrievable anchor 20 may comprise a self-expanding stent 20E having a proximal taper. This stent 20E is similar to the stent 20D described above with the exception of the proximal taper. The proximal taper on the stent 20E shown in FIG. 16E serves a similar function as the parachute-like tether 30 shown in FIG. 16D, but provides for a single attachment point for the tether 30. The tether 30 is connected to the proximal end of the tapered portion of the stent to facilitate collapse and retraction into the retrieval tube 128. The attachment point (i.e., tip) of the proximal taper may be concentric with the remainder of the structure as shown, or may be eccentric. An eccentric arrangement may promote more effective capture by biasing the tether 30 against the wall of the CV to thereby urge the lead electrode 14 against the CV wall.

Figure 17A:
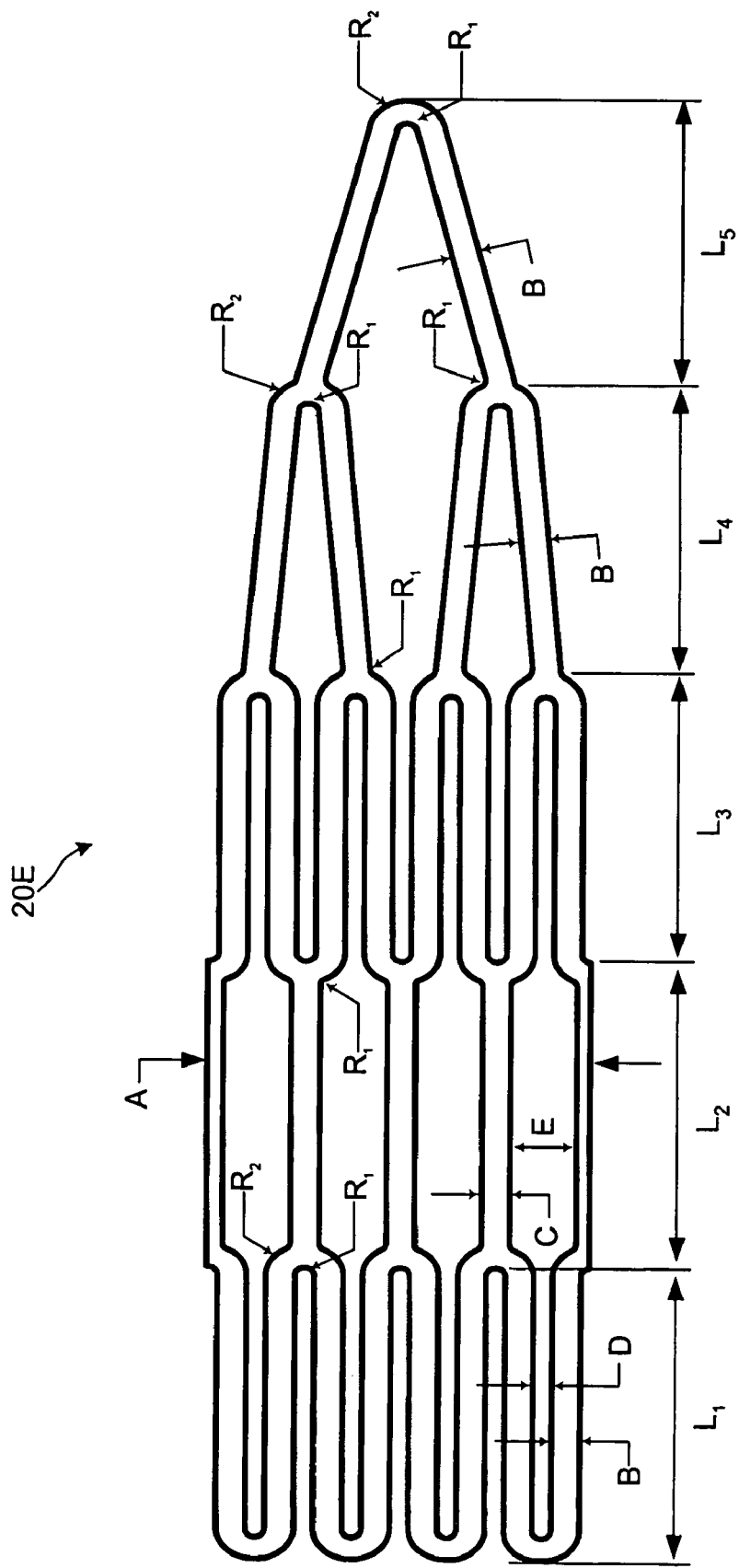
FIGS. 17A-17C are more detailed schematic illustrations of a retrievable anchor device in the form of a self-expandable stent.

FIG. 17A illustrates in more detail an example of a self-expanding stent 20E having a proximal taper. In this example, the stent 20E may be formed from Nitinol tubing commercially available from Nitinol Devices & Components, Inc. (NDC) with an inside diameter of approximately 0.024 inches and an outside diameter of 0.032 inches (NDC stock SE508). The tubing, the outer surface of which is shown in an unrolled state only for purposes of illustrating the pattern, may be cut into the desired pattern using laser cutting techniques employed by Laserage, Inc., for example. The pattern shown may have the following dimensions (inches): L1=0.150; L2=0.050; L3=0.150; L4=0.150; L5=0.150; A=0.100; B=0.0075; C=0.0075; D=0.005; E=0.0175; R1=0.0025; and R2=0.010.

After the desired pattern has been cut into the tube, the tube may be expanded into a stent 20E having an outside diameter of approximately 0.180 to 0.200 inches, for example. To effect expansion into the desired shape, the cut tubing may be placed on sequentially larger (e.g., steps of 0.030 inches) forming mandrels and briefly (e.g., 60 seconds) exposed to 500° C. The formed tubing may be given its final shape set for 4 minutes at 550 C., and then may be aged at 470 C. to provide a stent that has a martensite to austenite transformation which occurs over a relatively narrow temperature range (e.g. 15 centigrade degrees). After expanding and heat treating the cut tubing into a formed stent 20E, the stent may be grit-blasted and electro-polished to improve the mechanical integrity of the stent and smooth sharp edges.

Figure 17B:
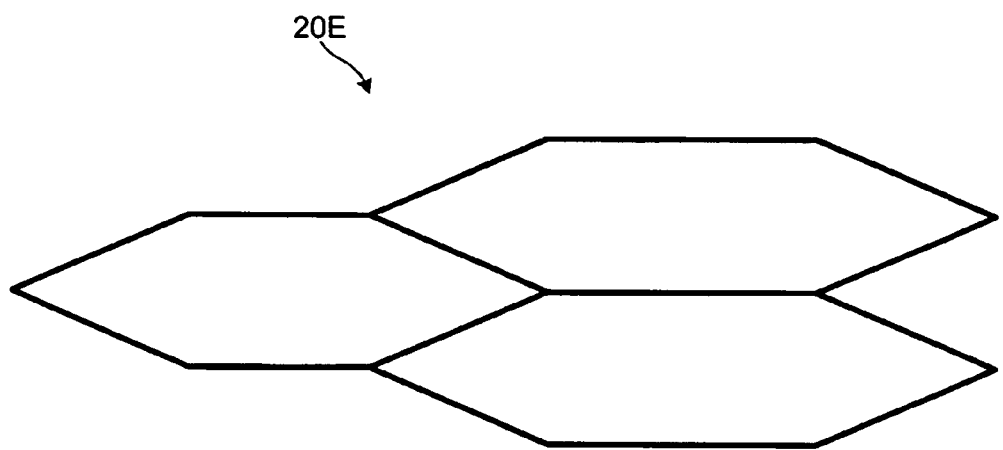
Figure 17C:
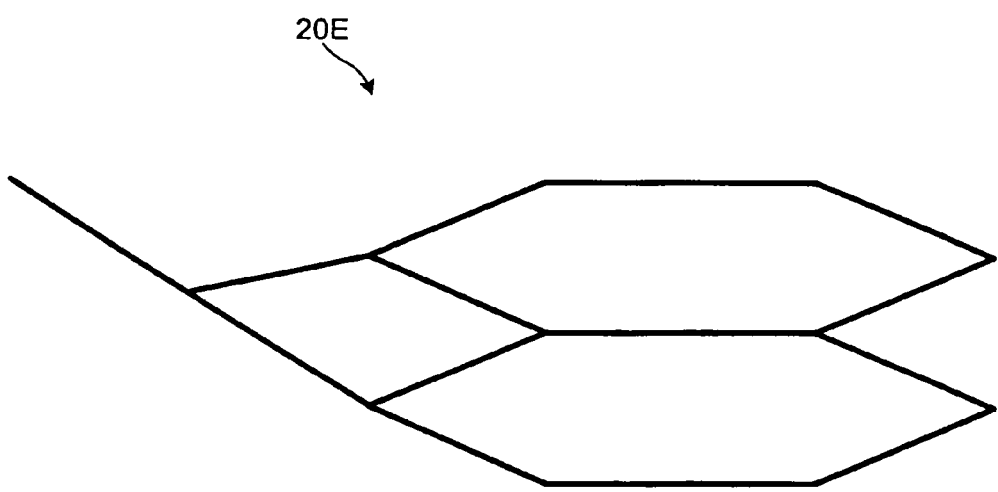

An example of a formed stent 20E is schematically shown in FIGS. 17B and 17C, which illustrate top and side views respectively, with the proximal end (for connection to the tether) shown to the left and the distal end shown to the right. As seen in FIG. 17B, the proximal portion of the stent 20E has a tapered structure to facilitate collapse of the stent 20E into a lumen of a delivery catheter (for removal or repositioning of the stent 20E) by pulling on the tether relative to the catheter. As seen in FIG. 17C, the proximal end of the stent 20E may be eccentrically disposed such that the tether and thus the lead electrodes lie against and establish good electrical contact with vascular or myocardial tissue.

All dimension of the stent 20E may be modified from the specific embodiment illustrated. For example, to avoid interference with lead placement, the stent 20E may have a length less than 1.0 inches, or less than 0.50 inches. To improve frictional anchoring by over-sizing, the stent anchor 20E may have an expanded diameter of preferably approximately 125% to 200% the inside diameter of the CV where the stent 20E is to be deployed.

Figure 18A:
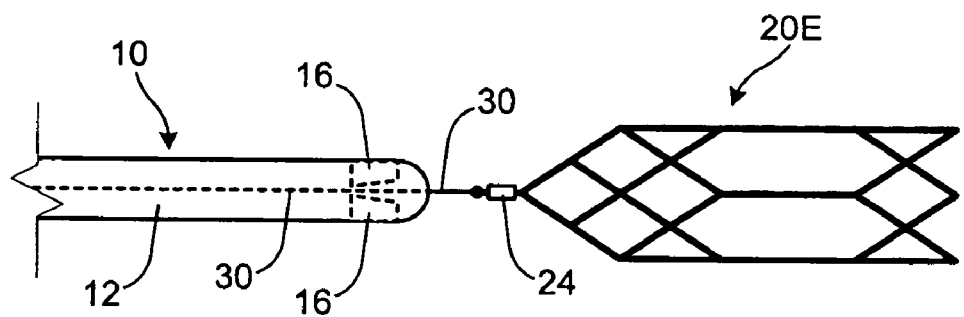
FIGS. 18A and 18B are schematic illustrations of an anchor used as a pacing electrode.
Figure 18B:
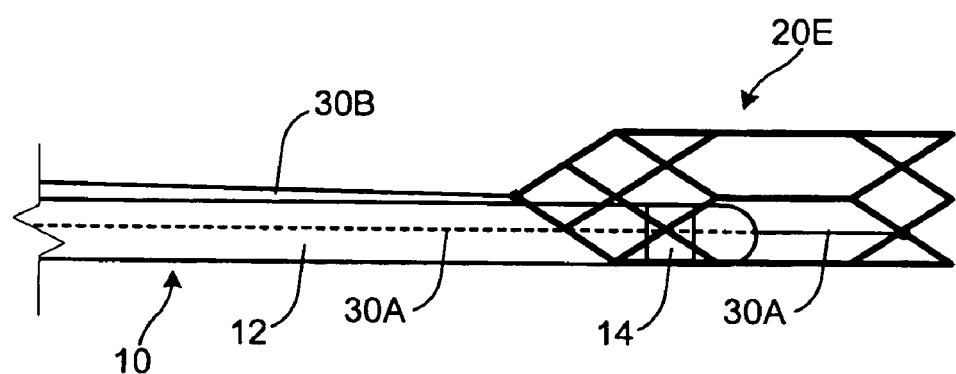

FIGS. 18A and 18B illustrate how a metallic anchor may be connected to a lead body and used as a pacing electrode. For sake of illustration, the anchor is shown to be a self-expanding stent anchor 20E with a proximal tapered portion to facilitate removal. All aspects of the anchor devices described with reference to FIGS. 3, 6 and 16A-16E may be applied to these embodiments. In the illustrated embodiments, the anchor may comprise a metallic structure to serve as an electrode and may be electrically connected to the conductors in the lead. Electrical contact between the anchor and the lead conductors may be provided internal to the lead as shown in FIG. 18A or external to the lead as shown in FIG. 18B.

With specific reference to FIG. 18A, the lead 10 may be modified to have internal electrical contacts 16 exposed to the guide wire lumen and electrically connected to wires extending proximally in the lead body 12. The stent anchor 20E may have a proximally disposed electrical contact 24 that is electrically connected to all or a select portion of the stent structure. The electrical contacts 16 are configured to electrically and mechanically engage with electrical contact 24 such that when the lead 10 is advanced distally, the internal electrical contacts 16 engage the stent contact 24 to establish electrical connection and mechanical lock. Because the stent anchor 20E serves as the pacing electrode, the conventional outer electrodes 14 on the lead may optionally be eliminated.

With reference to FIG. 18B, the conventional lead electrode(s) 14 establish direct contact with the inside of the stent structure 20E to provide and electrical connection therebetween. To facilitate this arrangement, the tether 30A may be connected to a distal strut of the stent structure 20E, extend inside the stent lumen, and pass through the guide wire lumen of the lead 10. With this arrangement, when the lead 10 is advanced distally, the lead electrode(s) 14 engage the exposed metallic stent structure 20E to establish electrical connection therebetween. To facilitate removal, a pull chord 30B may be connected to the proximal tip of the tapered portion of the stent anchor 20E.

Figure 19:
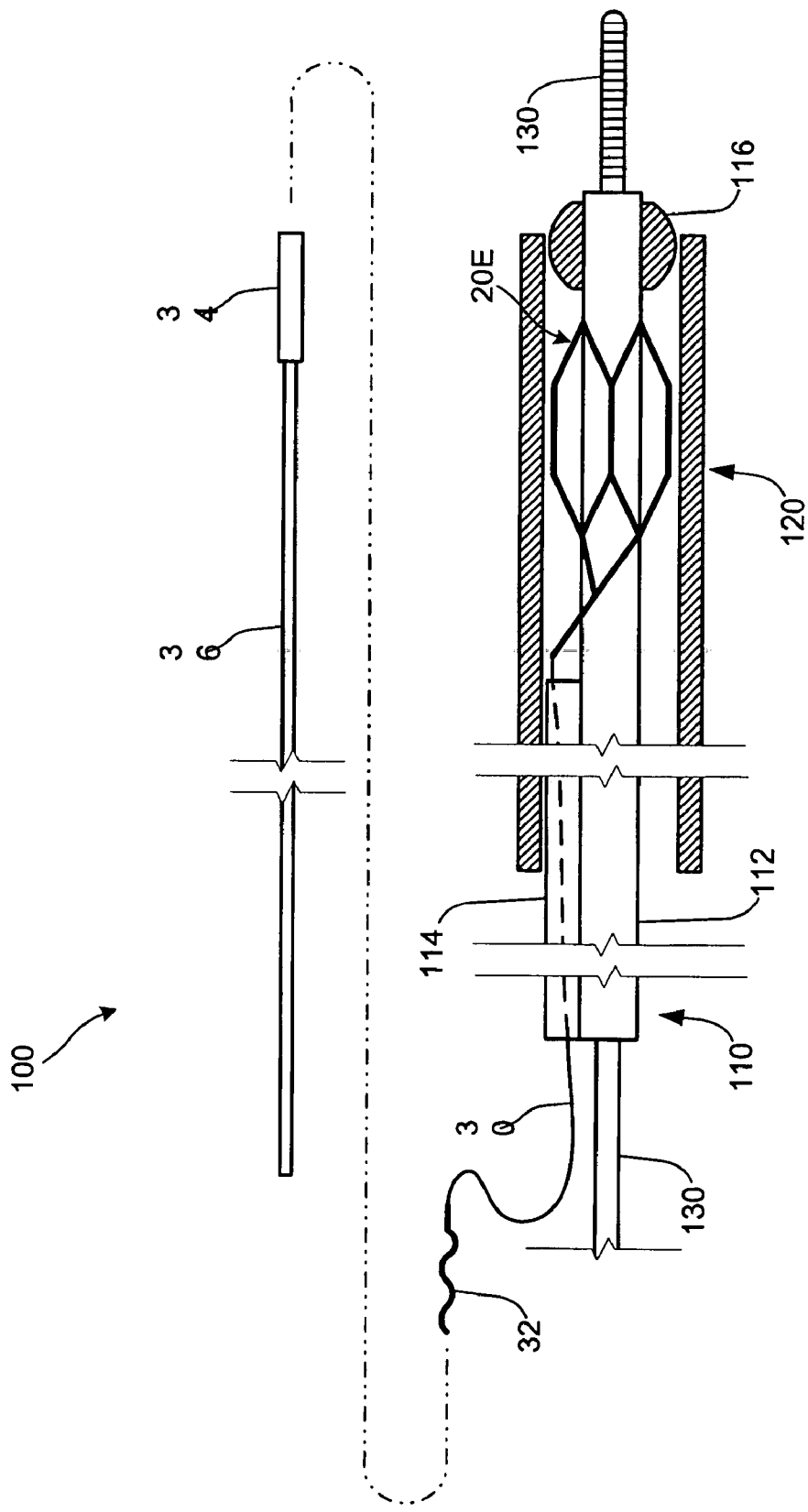
FIG. 19 is a schematic side view of an alternative anchor delivery system for use in delivering self-expanding stent anchor devices.

FIG. 19 illustrates an alternative anchor delivery catheter device 100, similar to the delivery device described with reference to FIG. 6. The delivery catheter 100 includes an inner tube 110 which extends through an outer tube 120. The inner tube 110 may include a guide wire lumen portion 112 and a coextending tether lumen portion 114. The inner tube may comprise a dual lumen extrusion or two tubes secured side-by-side, for example. The guide wire lumen portion 112 of the inner tube may be configured to contain a guide wire 130 extending therethrough. The tether lumen portion 114 of the inner tube may be configured to contain the tether 30 extending therethrough.

Stent anchor 20E is shown in a compressed condition inside the delivery catheter 100. Outer tube 120 maintains the stent anchor 20E in its compressed condition while the delivery catheter 100 is advanced to the desired site within the cardiac vasculature for deployment.

The guide wire lumen portion 112 may extend inside the compressed anchor 20E, and the tether lumen portion 114 may extend up to the proximal end of the stent anchor 20E adjacent the attachment point of the tether 30. A transition member 116 may be provided at or near the distal end of the guide wire lumen portion 112, which serves to diametrically transition the guide wire lumen portion 112 with the outer tube 120.

As depicted, prior to deployment of the anchor 20E, the proximal end of the inner tube 110 extends proximal of the proximal end of the outer tube 120. When it is desired to deploy anchor 20E, the outer tube 120 may retracted proximally relative to the inner tube 110, allowing the compressed anchor 20E to expand. After the anchor 20E is deployed, the outer tube 120 and inner tube 110 are withdrawn proximally (as well as the guide wire 130 if desired) relative to the anchor 20E and the tether 30, thus leaving the anchor 20E is place where deployed, with the tether 30 trailing behind.

When it is desired to advance an over-the-wire lead 10 over the tether 30 and into the vasculature, a leader 36 may be connected to the tether 30 by a connection mechanism. An example of a connection mechanism includes a tubular female receptacle 34, which mates with a male insert 32. Male insert 32 preferably includes curved regions that serve to increase the frictional engagement after the male insert 32 is position within the female receptacle 34. Other suitable connection mechanisms include those used for extending angioplasty guide wires, for example. After the lead 10 has been positioned in a desired portion of the vasculature, the connection 32/34 will be positioned proximal to the proximal end of the lead, and the connection 32/34 can thereafter be disconnected if desired.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method for stabilizing an electrical lead in a cardiac vein of a heart, comprising:

providing an electrical lead having a lumen extending from a proximal entry port to a distal exit port, the lead including one or more distal electrodes connected via wires in the lead to a pulse generator;

providing an elongate device including an expandable and retrievable stent anchor and an elongate tether comprising a polymeric multifilament structure, the elongate tether connected to the anchor and extending proximally from the anchor;

delivering the elongate device into the cardiac vein and deploying the stent anchor;

inserting a proximal end of the tether into the distal exit port of the lead;

advancing the lead over the tether into the cardiac vein such that the elongate tether extends through the lumen and the proximal entry port of the lead with the stent anchor disposed distally of the lead, and wherein the lead is longitudinally movable over the tether in the heart, and providing a connector and disposing the connector in the lumen of the lead adjacent the tether to limit longitudinal movement between the lead and the tether, wherein the expandable and retrievable stent anchor is expandable from a first delivery configuration to a second deployed configuration, wherein the second configuration is larger than the first configuration, and wherein the stent anchor includes a proximal taper and a proximal eccentric apex configured to facilitate retrieval into a tube, wherein the tether is connected to the apex and wherein the step of deploying the stent anchor comprises deploying the stent anchor such that the one or more distal electrodes of the lead lie against and establish electrical contact with tissue of the heart.

2. A method for stabilizing an electrical lead in a cardiac vein of a heart, comprising:

providing an electrical lead having a lumen extending from a proximal entry port to a distal exit port, the lead including one or more distal electrodes connected via wires in the lead to a pulse generator;

providing an elongate device including an expandable anchor and an elongate tether comprising a polymeric multifilament structure, the elongate tether connected to the anchor and extending proximally from the anchor;

delivering the elongate device into the cardiac vein and deploying the anchor;

inserting a proximal end of the tether into the distal exit port of the lead;

advancing the lead over the tether into the cardiac vein such that the elongate tether extends through the lumen and the proximal entry port of the lead with the anchor disposed distally of the lead, wherein the lead is longitudinally movable over the tether in the heart; and securing the lead to the elongate device to limit longitudinal movement therebetween;

wherein the expandable and retrievable anchor is expandable from a first delivery configuration to a second deployed configuration, wherein the second configuration is larger than the first configuration, and wherein the anchor includes a proximal taper and a proximal eccentric apex configured to facilitate retrieval into a tube, wherein the tether is connected to the apex and wherein the step of deploying the anchor comprises deploying the anchor such that the one or more distal electrodes of the lead lie against and establish electrical contact with tissue of the heart.

* * * * *